(12) United States Patent
Coope et al.

(10) Patent No.: US 8,185,315 B2
(45) Date of Patent: *May 22, 2012

(54) DETERMINATION OF IRREDUCIBLE WATER CUT-OFF USING TWO DIMENSIONAL NUCLEAR MAGNETIC RESONANCE DATA

(75) Inventors: Daniel F. Coope, Annapolis, MD (US); Osamah Gh. A. Gh. Albannaw, Salwa (KW)

(73) Assignee: Baker Hughes Incorporated, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/040,381

(22) Filed: Mar. 4, 2011

(65) Prior Publication Data

US 2011/0153216 A1    Jun. 23, 2011

Related U.S. Application Data

(63) Continuation of application No. 12/055,678, filed on Mar. 26, 2008, now Pat. No. 7,917,294.

(51) Int. Cl.
*G01V 3/32*    (2006.01)
*G01V 3/38*    (2006.01)

(52) U.S. Cl. .......................................... 702/13; 324/303

(58) Field of Classification Search .................... 702/13, 702/12; 324/300, 303
See application file for complete search history.

(56) References Cited

U.S. PATENT DOCUMENTS

| 5,497,087 | A | 3/1996 | Vinegar et al. |
| 5,498,960 | A * | 3/1996 | Vinegar et al. ................. 324/303 |
| 5,696,448 | A | 12/1997 | Coates et al. |
| 5,838,155 | A | 11/1998 | Bowers |
| 6,833,698 | B2 | 12/2004 | Sun et al. |
| 2003/0214287 | A1 | 11/2003 | Sun et al. |
| 2009/0189604 | A1* | 7/2009 | Romero ......................... 324/303 |

OTHER PUBLICATIONS

Chen, S., et al., MR Explorer Log Acquisition Methods: Petrophysical Object-Oriented Approach, paper ZZ, 44th Annual Symposium and Exhibition, Galveston, TX, Jun. 2003.
International Search Report and Written Opinion, Mailed Oct. 27, 2009, International Application No. PCT/US2009/038313, Written Opinion 7 Pages, International Search Report 3 Pages.

* cited by examiner

*Primary Examiner* — Bryan Bui
(74) *Attorney, Agent, or Firm* — Cantor Colburn LLP

(57) ABSTRACT

A method for estimating a distribution of pore sizes of a fluid filled rock formation penetrated by a borehole, the method includes: processing nuclear magnetic resonance (NMR) data to determine a distribution of diffusion coefficients and a distribution of relaxation time constants for at least one depth in the borehole; plotting the distribution of diffusion coefficients and the distribution of relaxation time constants as a cross-plot for the at least one depth; identifying a water line on the cross-plot, each point on the water line having substantially the same value for the diffusion coefficient; and estimating the distribution of pore sizes from the distribution of relaxation time constants plotted along the water line.

12 Claims, 6 Drawing Sheets

DETERMINATION OF IRREDUCIBLE WATER CUT-OFF USING TWO DIMENSIONAL NUCLEAR MAGNETIC RESONANCE DATA

This application is a continuation of U.S. patent application Ser. No. 12/055,678 filed on Mar. 26, 2008, now U.S. Pat. No. 7,917,294, the entire contents of which are incorporated herein by reference.

BACKGROUND OF THE INVENTION

1. Field of the Invention

This invention relates to the field of nuclear magnetic resonance (NMR) well logging apparatus and methods. More specifically, the invention is related to methods for processing NMR signals to determine fluid and gas properties, relative and total amounts of fluids, and the ability to produce these fluids in fluid-bearing earth formations penetrated by wellbores. Additionally, the pore size distribution of the porous rock containing these fluids is estimated.

2. Description of the Related Art

Downhole characterization techniques are of considerable value for geophysical exploration. For example, characterization of parameters associated with fluid-bearing earth formations provides insight into quantifying hydrocarbons and water present in the formation. A number of technologies are applied to determine the parameters. These technologies include nuclear magnetic resonance (NMR) imaging. An apparent transverse relaxation time constant distribution may be used to analyze water, oil and gas zones.

When a reservoir rock, clastic or carbonate, is completely filled with water, a distribution of apparent transverse relaxation time constants ($T_{2,app}$) will reflect the pore size distribution of the rock due to interaction with the rock surface. This interaction is referred to as surface transverse relaxation and is measured by a surface transverse relaxation time constant ($T_{2,surf}$). Often rock samples are saturated with water in a laboratory to determine the value of $T_{2,app}$ that separates the irreducible water in the reservoir from the water that can be produced when the rock is in-situ under normal production conditions. That value of $T_{2,app}$ may be referred to as irreducible water cut-off (or "COBVI"). FIG. 1 is a graph of incremental porosity versus $T_{2,app}$. Referring to FIG. 1, the COBVI value of $T_{2,app}$ is depicted along with a value of $T_{2,app}$ ("COCBW") that separates clay bound water from the irreducible water.

However, in reservoirs determining COBVI is complicated by the presence of hydrocarbon. Both oil and gas respond differently than water to the NMR measurements. The oil and gas respond differently because, unlike water, the oil and gas generally do not exhibit surface transverse relaxation. It is presumed that the oil and gas do not contact the water-wet rock. In the case of oil and gas containing reservoirs, the hydrocarbon NMR signals interfere with the $T_{2,app}$ of water and, therefore, interfere with determining pore size distribution. The interference is an acute problem in carbonate rocks where the COBVI is highly variable and the $T_{2,app}$ signal from oil and gas often occurs within the $T_{2,app}$ signal for the irreducible water.

Therefore, what are needed are techniques for removing the oil and gas NMR signals from the distribution of apparent transverse relaxation time constants.

BRIEF SUMMARY OF THE INVENTION

Disclosed is one example of a method for estimating a distribution of pore sizes of a water and hydrocarbon filled rock formation penetrated by a borehole, the method includes: processing nuclear magnetic resonance (NMR) data to determine a distribution of diffusion coefficients and a distribution of relaxation time constants for the water and hydrocarbon filled rock formation for at least one depth in the borehole; plotting the distribution of diffusion coefficients and the distribution of relaxation time constants as a cross-plot for the at least one depth; identifying a water line on the cross-plot, each point on the water line having substantially the same value for the diffusion coefficient; and estimating the distribution of pore sizes from the distribution of relaxation time constants plotted along the water line.

Also disclosed is an embodiment of an apparatus for estimating a distribution of pore sizes of a water and hydrocarbon filled rock formation penetrated by a borehole, the apparatus includes an electronics unit for: processing nuclear magnetic resonance (NMR) data to determine a distribution of diffusion coefficients and a distribution of relaxation time constants for the water and hydrocarbon filled rock formation for at least one depth in the borehole; plotting the distribution of diffusion coefficients and the distribution of relaxation time constants as a cross-plot for the at least one depth; identifying a water line on the cross-plot, each point on the water line having substantially the same value for the diffusion coefficient; and estimating the distribution of pore sizes from the distribution of relaxation time constants plotted along the water line.

Further disclosed is a non-transitory computer readable medium having computer executable instructions for estimating a distribution of pore sizes of a water and hydrocarbon filled rock formation by implementing a method that includes: processing nuclear magnetic resonance (NMR) data to determine a distribution of diffusion coefficients and a distribution of relaxation time constants for the water and hydrocarbon filled rock formation for at least one depth in the borehole; plotting the distribution of diffusion coefficients and the distribution of relaxation time constants as a cross-plot for the at least one depth; identifying a water line on the cross-plot, each point on the water line having substantially the same value for the diffusion coefficient; estimating the distribution of pore sizes from the distribution of relaxation time constants plotted along the water line; and at least one of recording the distribution of pore sizes and displaying the distribution of pore sizes to a user.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

DETAILED DESCRIPTION OF THE INVENTION

Figure 1:
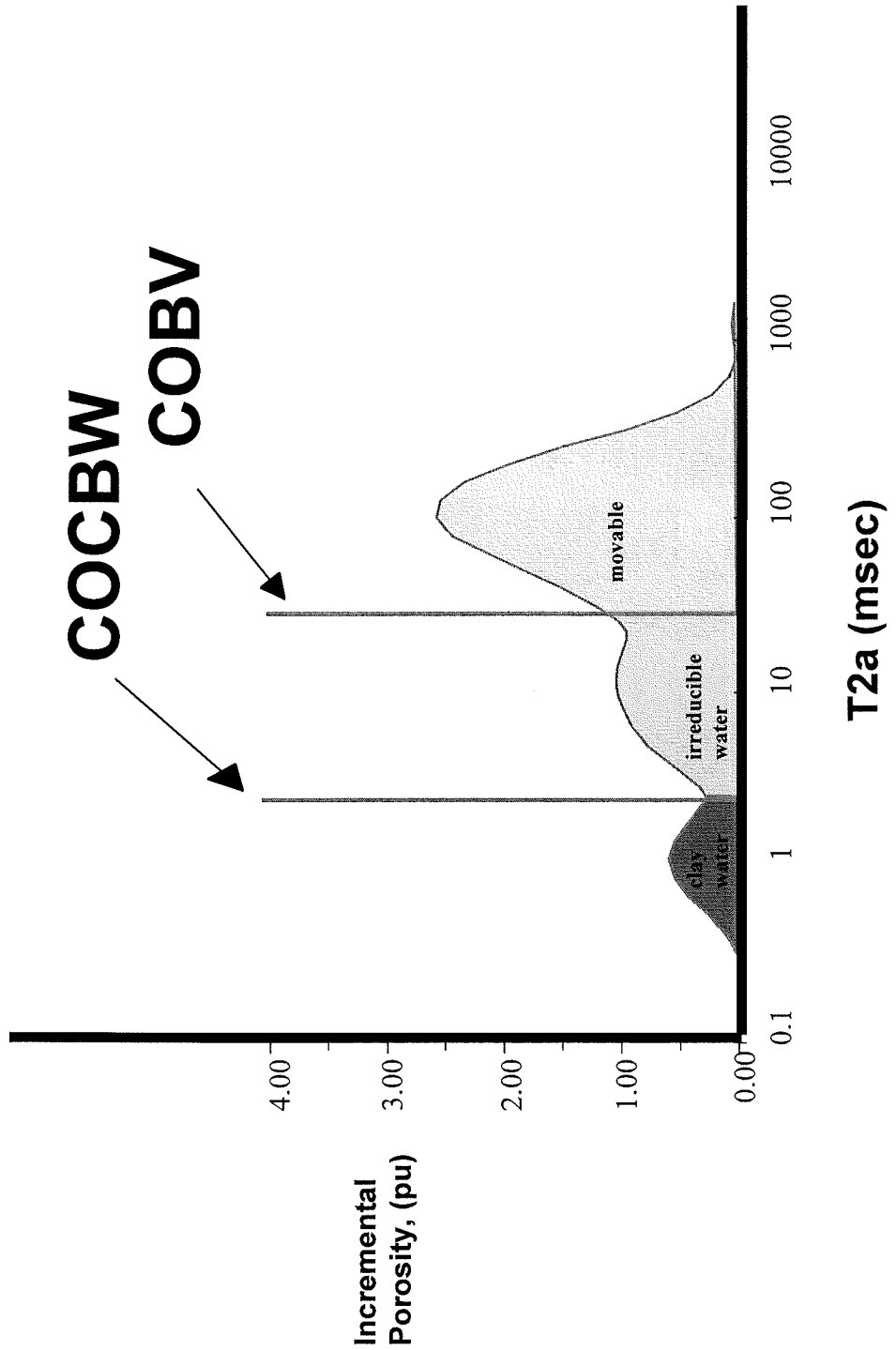
FIG. 1 is a graph of incremental porosity versus apparent transverse relaxation time constant.

Disclosed are exemplary techniques for estimating petrophysical properties of a fluid-filled rock formation and the fluids therein. The techniques use two-dimensional nuclear magnetic resonance (NMR) measurements to obtain NMR data from the rock formation. The techniques, which include a method and apparatus, are used to process the NMR data to remove hydrocarbon NMR signals. Once the hydrocarbon NMR signals are removed, the remainder of the NMR data can be used to determine several petrophysical properties. These properties include irreducible water volume and permeability. One benefit of these techniques is that the techniques may be used to analyze rocks that are only partially water-wet.

For convenience, certain definitions are presented for use throughout the specification. The term "rock" relates to a porous matrix that contains a fluid. The term "transverse relaxation time constant" ($T_2$) relates to the time required for a transverse magnetization vector in a material to drop to 37% of its original amplitude. The transverse relaxation time constant reflects the rate of transverse energy loss through a spin-spin relaxation created by a perturbing radio frequency pulse that may be referred to as a Carr-Purcell-Meiboom-Gill pulse or "CPMG pulse." The term "apparent transverse relaxation time constant" ($T_{2,app}$) relates to the transverse relaxation time constant measured in the NMR measurements. The apparent transverse relaxation time constant may include a surface component, a bulk (or intrinsic) component, and a diffusive component. The term "wetting" relates to the contact between a solid and a liquid resulting from intermolecular interactions when the solid and the liquid are brought together. The term "BVI" relates to bulk volume irreducible or the volume of irreducible water. The term "COBVI" relates to cut-off of BVI or the value of $T_2$ that separates movable fluid from irreducible water. The term "COCBW" relates to cut-off of clay bound water or the value of $T_2$ that separates clay bound water from irreducible water. The term "movable fluid" relates to fluid in a reservoir that can be removed from a wellbore. The term "irreducible fluid" relates to the lowest saturation of water (or the least amount of water) in a reservoir that can be achieved by displacing the water with oil or gas. The term "flushed zone" relates the volume close to the borehole wall in which it is assumed all of the movable fluids have been displaced by mud filtrate. The term "API" relates to specifications established by the American Petroleum Institute.

As a matter of convention, one should note that the variables used herein appear throughout the disclosure. Accordingly, previously defined variables are generally not reintroduced. For convenience of referencing, some of the following representations are applied herein, or related to the teachings herein:

$T_2$—transverse relaxation time constant
$T_{2,app}$—apparent transverse relaxation time constant
$T_{2,int}$—intrinsic relaxation time constant component for $T_{2,app}$
$T_{,surf}$—surface relaxation time constant component for $T_{2,app}$
$T_{2,diff}$—diffusion relaxation time constant component for $T_{2,app}$
G—magnetic field gradient
γ—gyromagnetic ratio
TE—inter-echo time between radio frequency pulses The apparent transverse relaxation time constant ($T_{2,app}$) is related to an intrinsic transverse relaxation time constant ($T_{2,int}$) and a diffusion transverse relaxation time constant ($T_{2,diff}$) according to equation (1).

$$\frac{1}{T_{2,app}} = \frac{1}{T_{2,int}} + \frac{1}{T_{2,diff}} \quad (1)$$

The diffusion transverse relaxation time constant ($T_{2,diff}$) can be related to a diffusion coefficient D according to equation (2).

$$\frac{1}{T_{2,diff}} = \frac{\gamma^2 G^2 D \cdot TE^2}{12} \quad (2)$$

Using data processing techniques known in the art of NMR well logging, both $T_{2,int}$ and D may be determined for each depth in a borehole (or well bore) that NMR measurements are performed.

Figure 2:
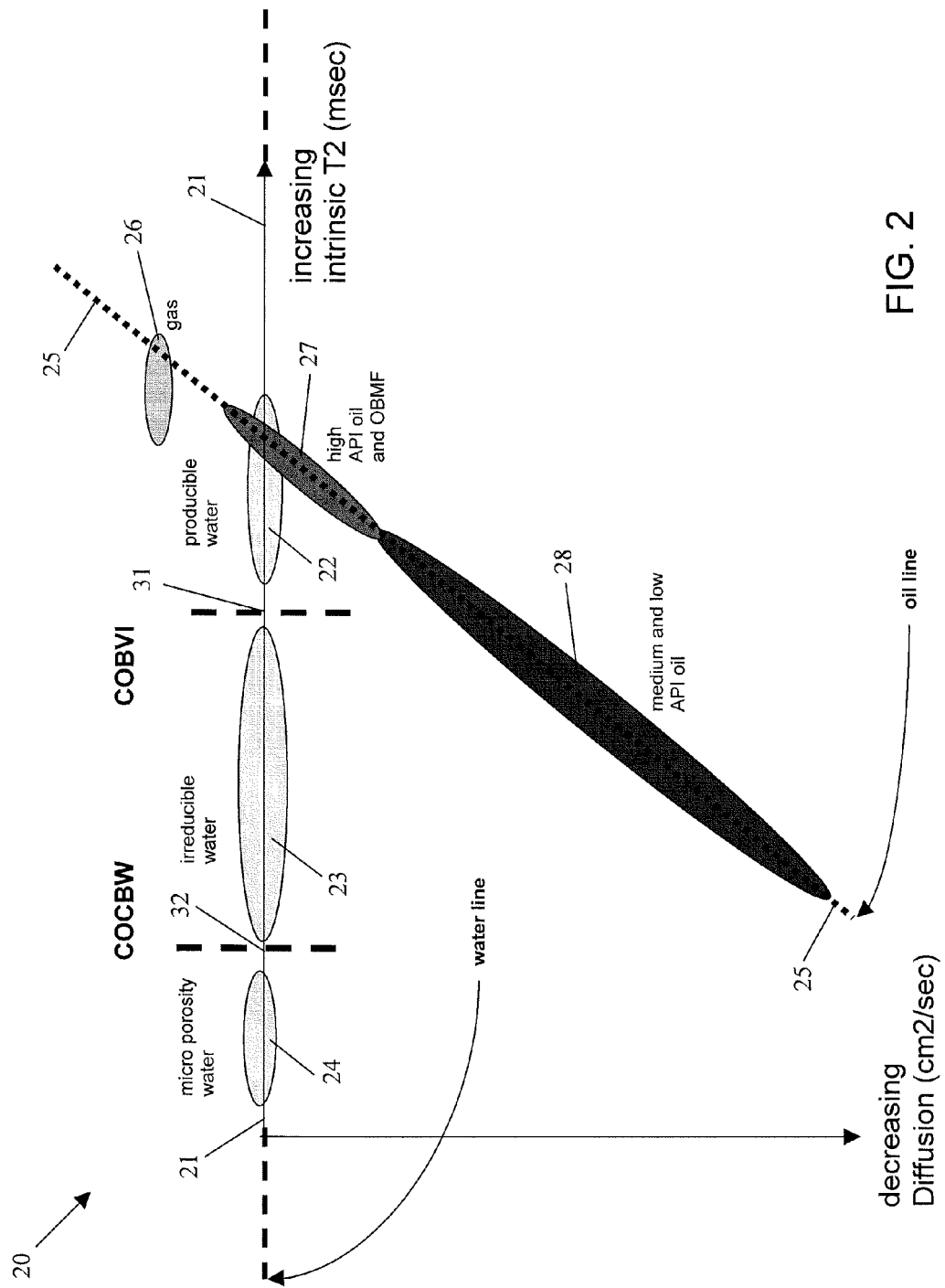
FIG. 2 is a cross-plot of diffusion versus intrinsic transverse relaxation time constant.

In one embodiment of the method, the two-dimensional NMR measurements are performed at a plurality of depths in the well bore. The NMR data is processed to determine values of D and $T_{2,int}$ for each depth in the plurality of depths. Next, D and $T_{2,int}$ are plotted on a graph known as a "cross-plot." FIG. 2 illustrates an exemplary embodiment of a cross-plot 20 for a certain depth in the well bore. FIG. 2 shows a water line 21 that intersects a producible water data point group 22, an irreducible water data point group 23, and a micro-porosity water data point group 24. The points of the water line 21 include about the same value of the diffusion coefficient D. Note that the terms "micro-porosity," "meso-porosity" and "macro-porosity," generally used in carbonate analysis, are more general terms for clay, irreducible and producible respectively, which are more particular to clastic rock analysis.

The NMR signals due to water (i.e., data point groups 22, 23 and 24) are plotted along the waterline 21. The data point groups 22, 23 and 24, along the water line 21, are particular to water at the reservoir conditions of temperature, pressure, and salinity.

Referring to FIG. 2, an oil line 25 is also illustrated. In general, the oil line 25 includes a set of points in which $T_{2,int}$ increases as D increases (i.e., the oil line 25 has a positive slope). In the example of FIG. 2, the oil line 25 intersects a high API oil (and oil-based mud filtrate) data point group 27, and a medium and low API oil data point group 28. A gas data point group 26 does not necessarily follow this relationship. The data point groups 26, 27 and 28 are particular to hydrocarbons at reservoir conditions.

Referring to FIG. 2, note that most oil and gas NMR signals are not included in the distribution of $T_{2,int}$ along the water line 21. It follows that the distribution of $T_{2,int}$ along the water line 21 represents the pore size distribution of the small and intermediate size pores in the rock, partially excluding those largest pores that contain hydrocarbon. Referring again to FIG. 2, a COBVI cut-off point 31 and a COCBW cut-off point 32 are depicted on the water line 21.

Figure 3:
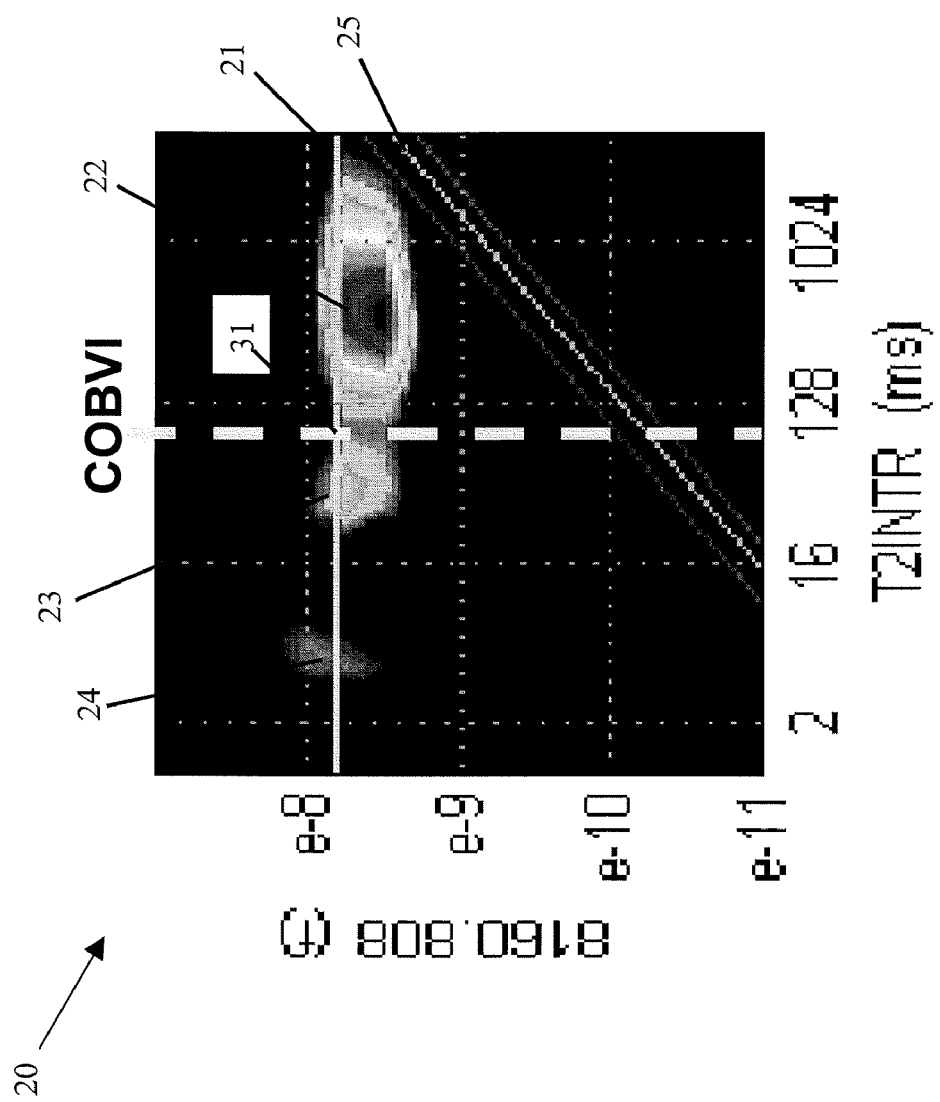
FIG. 3 illustrates an example of a diffusion versus intrinsic transverse relaxation time constant cross-plot.

FIG. 3 is a cross-plot of D versus $T_{2,int}$ derived from NMR data obtained from a well bore at a depth of about 8160 feet.

Several methods are presented next for determining various petrophysical properties from the cross-plot 20. The COBVI cut-off point 31 may be estimated as a point on the water line 21 between the irreducible water data point group 23 and the producible water data point group 22.

The irreducible water volume and the clay bound water volume about the depth at which an NMR measurement was performed may be estimated by integrating $T_{2,int}$ along the water line 21 for values of $T_{2,int}$ less than the COBVI cut-off point 31. Above a hydrocarbon-to-water contact depth in a reservoir, the bulk water volume may be estimated by summing integrations of $T_{2,int}$ along the water line 21 for values of $T_{2,int}$ less than the COBVI cut-off point 31 for each depth NMR data obtained from the reservoir at and/or above the contact depth.

The free fluid volume about a depth at which NMR data was obtained may be estimated by integrating $T_{2,int}$ for values of $T_{2,int}$ greater than the COBVI cut-off point 31 for all values of D.

The volume of oil (may be heavy and/or light oil) in a flushed zone about a depth at which NMR data was obtained may be estimated by integrating $T_{2,int}$ along the oil line 25. Above a hydrocarbon-to-water contact depth in a reservoir, hydrocarbon volume may be estimated by summing integrations of $T_{2,int}$ along the oil line 25, except for any intersections with data point groups 22, 23 and 24, for each depth NMR data was obtained from the reservoir at and/or above the contact depth.

In heavy oil reservoirs where the heavy oil is assumed not to be moved by invasion of water or oil-based mud filtrates, the oil volume about a depth at which NMR data was obtained may be estimated by integrating $T_{2,int}$ along the oil line 25. The total oil volume in these reservoirs may be estimated by summing integrations of $T_{2,int}$ along the oil line 25 for each depth NMR data was obtained from the reservoir.

The permeability of a rock formation at a depth at which NMR data was obtained may be estimated from the distribution of $T_{2,int}$ along the water line 21.

Established petrophysical techniques may be used in conjunction with the methods presented above. These established techniques use data from "conventional" measurements that include logs of resistivity, neutron, density, and gamma ray in addition to wireline formation pressures and samples, and retrieved cores. With the methods presented above, the established techniques, and the addition of geological models and seismic cross sections, additional petrophysical parameters and/or refinements to pre-determined petrophysical parameters may be estimated.

For example, when oil-based mud is used to drill a well, oil-based mud filtrate (obmf) will fill movable oil and water pore space and, thus, making separation of the movable fluid (oil and obmf) from the irreducible water obvious on the distribution of $T_{2,int}$ along the water line 21. Therefore, estimating the COBVI cut-off point 31 will also be obvious.

As another example, using NMR measurements and other logs it is possible to select a zone of the reservoir that contains only water. When a 100 percent water filled zone is identified, the $T_{2,int}$ distribution along the water line 21 will reveal peaks representing micro-porosity, meso-porosity, and macro-porosity in many rocks, especially carbonates. These peaks will be recognized using the methods presented above and the established petrophysical techniques as representing the free water and the irreducible water separated by the COBVI cut-off point 31.

Another practice that can be used with the methods presented above is to extrapolate results of analysis of reservoir intervals (or zones) to adjacent or nearby zones. For example, using conventional wireline formation test and resistivity logs, zones in a reservoir that are effectively impermeable can be identified. These zones can be assumed to contain only un-filtrated fluids. In this case, it will often be possible to identify the water represented by the distribution of $T_{2,int}$ along the water line 21 because the water in this case is by definition irreducible. The COBVI cut-off point 31 can be identified and applied to other permeable, petrophysically and geologically similar, zones in the reservoir.

As another example, from observation of the distribution of $T_{2,int}$ along the water line 21, the COBVI cut-off point 31 can be estimated and tested against other reservoir conditions, such as information that the reservoir does not produce water from the interval in which the NMR data was obtained. This information enables selecting the COBVI cut-off point 31 that is invariant throughout the reservoir or set of reservoirs.

Figure 4:
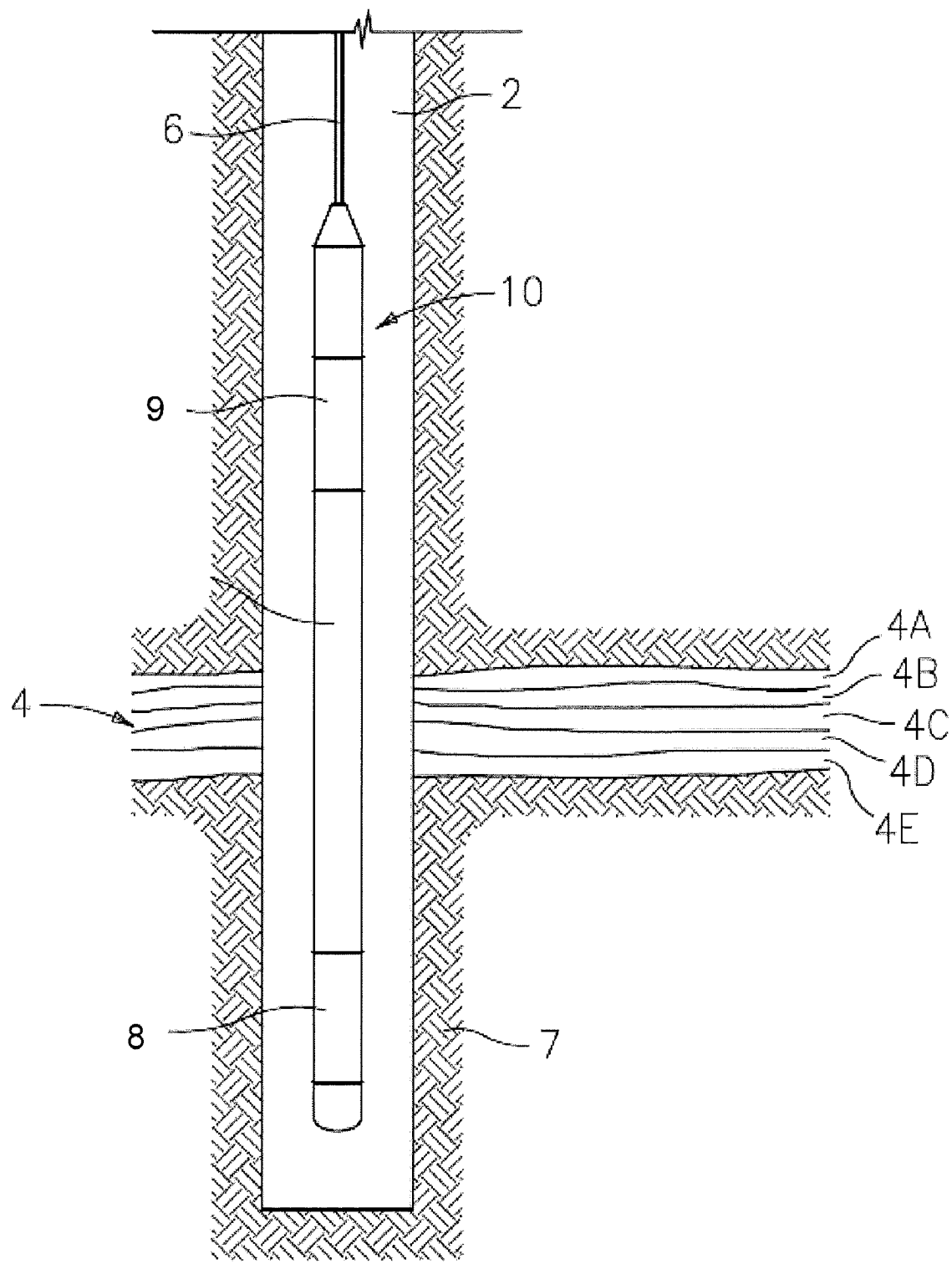
FIG. 4 illustrates an exemplary embodiment of a logging instrument in a borehole penetrating the earth.

Apparatus for implementing the teachings herein is now presented. Referring to FIG. 4, an embodiment of a well logging instrument 10 is shown disposed in a borehole 2. The borehole 2 is drilled through earth 7 and penetrates formations 4, which include various formation layers 4A-4E. The logging instrument 10 is typically lowered into and withdrawn from the borehole 2 by use of an armored electrical cable 6 or similar conveyance as is known in the art. The formations 4 can be rock that includes a porous matrix filled with a formation fluid. In the embodiment of FIG. 4, the logging instrument 10 includes an NMR instrument 8 for performing the NMR measurements and an electronics unit 9 for processing the NMR measurements (or data from the NMR measurements). The NMR instrument 8 includes components for performing the NMR measurements such as a magnet and an antenna for example. Recording distributions of $T_{2,app}$, $T_{2,int}$, and D at various depths in the borehole 2 are examples of processing the NMR measurements. Further, the electronic unit 9 can be used to estimate various petrophysical properties from the distributions.

For the purposes of this discussion, the borehole 2 is depicted in FIG. 4 as vertical and the formations 4 are depicted as horizontal. The apparatus and method however can be applied equally well in deviated or horizontal wells or with the formation layers 4A-4E at any arbitrary angle. The apparatus is equally suited for performing NMR measurements and processing NMR data in wireline applications and logging-while-drilling (LWD) applications. In LWD applications, the logging instrument 10 may be disposed in a drilling collar.

Figure 5:
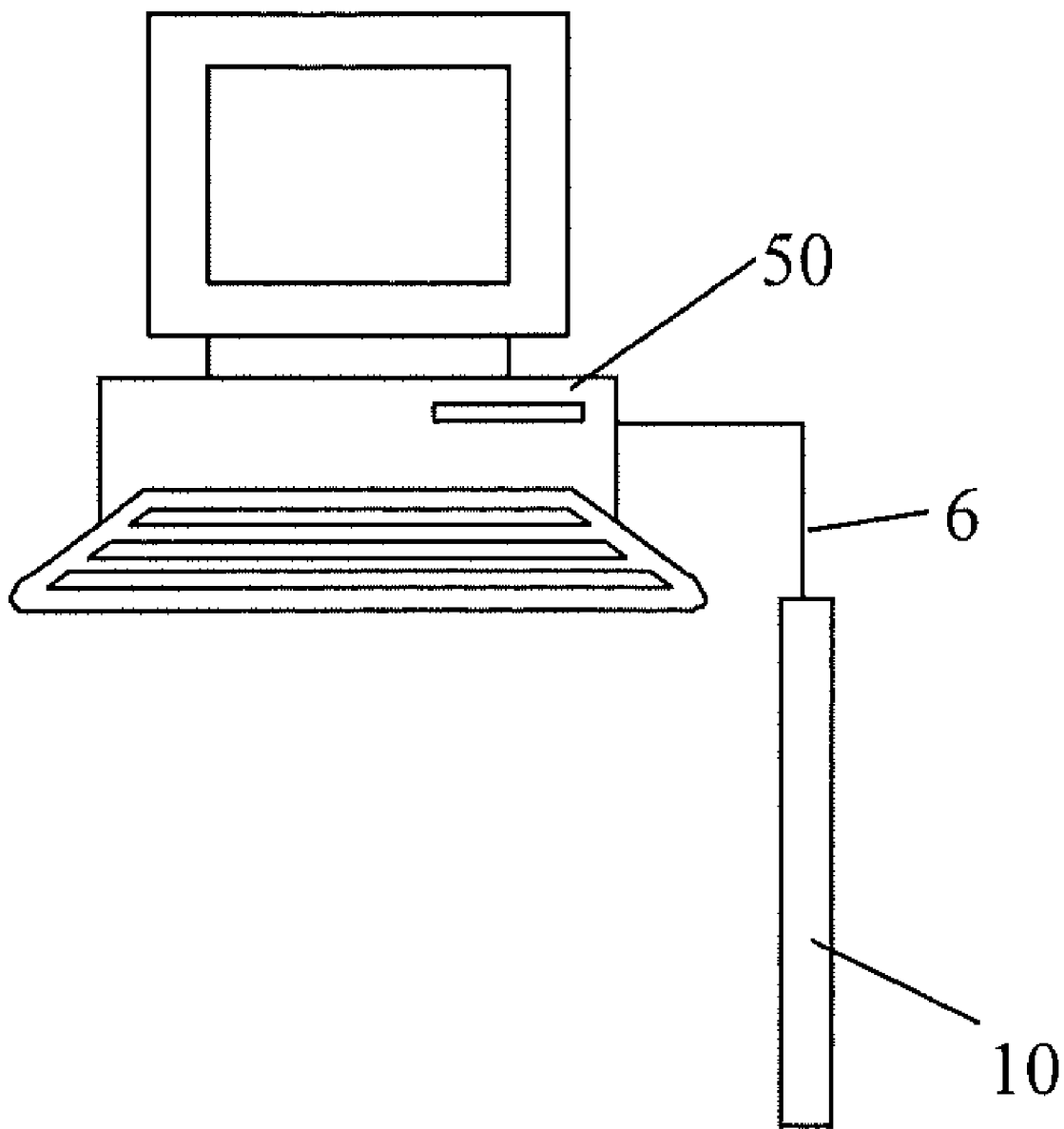
FIG. 5 illustrates a processing system coupled to the logging instrument.

Referring to FIG. 5, another apparatus for implementing the teachings herein is depicted. In FIG. 5, the apparatus includes a computer 50 coupled to the logging instrument 10. Exemplary components include, without limitation, at least one processor, storage, memory, input devices, output devices and the like. As these components are known to those skilled in the art, these are not depicted in any detail herein. The computer 50 may be disposed at least one of at the surface of the earth 7 and in the instrument 10. The computer 50 may also be incorporated into the electronics unit 9.

Generally, some of the teachings herein are reduced to an algorithm that is stored on machine-readable media. The algorithm is implemented by the computer 50 and provides operators with desired output.

Figure 6:
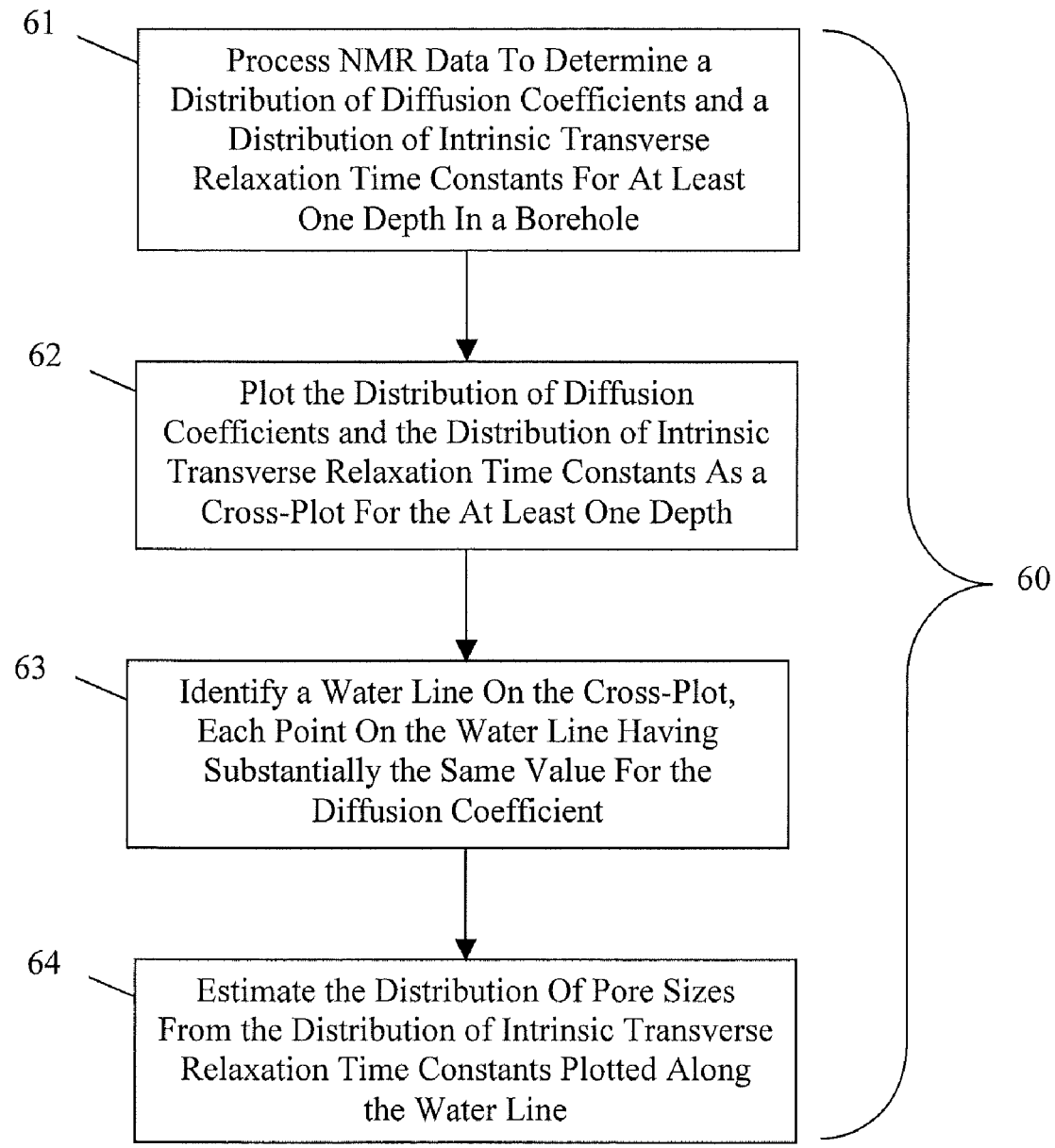
FIG. 6 presents an example of a method for estimating irreducible water cut-off.

FIG. 6 presents one example of a method 60 for estimating a distribution of pore sizes of a fluid filled rock formation. The method 60 calls for (step 61) processing NMR data to determine a distribution of diffusion coefficients D and a distribution of intrinsic transverse relaxation time constants $T_{2,int}$ for at least one depth in the borehole 2. Further, the method 60 calls for (step 62) plotting the distribution of diffusion coefficients D and the distribution of intrinsic transverse relaxation time constants $T_{2,int}$ as the cross-plot 20 for the at least one depth. Further, the method 60 calls for (step 63) identifying the water line 21 on the cross-plot, each point on the water line 21 having substantially the same value for the diffusion coefficient D. Further, the method 60 calls for (step 64) estimating the distribution of pore sizes from the distribution of intrinsic transverse relaxation time constants $T_{2,int}$ plotted along the water line.

The embodiments of the teachings presented above use a distribution of transverse relaxation time constants to estimate a distribution of pore sizes of a fluid filled rock formation and other parameters. Other embodiments of the teachings herein call for using a distribution of longitudinal relaxation time constants $T_1$ in place of or in addition to the distribution of transverse relaxation time constants.

In support of the teachings herein, various analysis components may be used, including digital and/or analog systems. The digital and/or analog systems may be included in the electronic unit 9 for example. The system may have components such as a processor, analog to digital converter, digital to analog converter, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing aspects of the teachings herein. For example, a power supply (e.g., at least one of a generator, a remote supply and a battery), cooling component, heating component, motive force (such as a translational force, propulsional force, or a rotational force), digital signal processor, analog signal processor, sensor, magnet, antenna, transmitter, receiver, transceiver, controller, optical unit, electrical unit or electromechanical unit may be included in support of the various aspects discussed herein or in support of other functions beyond this disclosure.

Elements of the embodiments have been introduced with either the articles "a" or "an." The articles are intended to mean that there are one or more of the elements. The terms "including" and "having" are intended to be inclusive such that there may be additional elements other than the elements listed.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a distribution of pore sizes of a water and hydrocarbon filled rock formation penetrated by a borehole, the method comprising:
   processing nuclear magnetic resonance (NMR) data to determine a distribution of diffusion coefficients and a distribution of relaxation time constants for the water and hydrocarbon filled rock formation for at least one depth in the borehole;
   plotting the distribution of diffusion coefficients and the distribution of relaxation time constants as a cross-plot for the at least one depth;
   identifying a water line on the cross-plot, each point on the water line having substantially the same value for the diffusion coefficient; and
   estimating the distribution of pore sizes from the distribution of relaxation time constants plotted along the water line.

2. The method of claim 1, wherein the relaxation time constants comprise transverse relaxation time constants.

3. The method of claim 2, further comprising determining a transverse relaxation time constant (COCBW) that separates clay bound water from irreducible water.

4. The method of claim 2, further comprising determining a transverse relaxation time constant (COBVI) that separates irreducible water from movable water.

5. The method of claim 4, further comprising determining free fluid volume by integrating an intrinsic transverse relaxation time constant component of the transverse relaxation time constant for values of the intrinsic transverse time constant component greater than COBVI for all values of the diffusion coefficient.

6. The method of claim 1, wherein the relaxation time constants comprise longitudinal relaxation time constants.

7. The method of claim 1, wherein the distribution of relaxation time constants is a distribution of intrinsic transverse relaxation time constants.

8. An apparatus for estimating a distribution of pore sizes of a water and hydrocarbon filled rock formation penetrated by a borehole, the apparatus comprising:
   an electronics unit for:
      processing nuclear magnetic resonance (NMR) data to determine a distribution of diffusion coefficients and a distribution of relaxation time constants for the water and hydrocarbon filled rock formation for at least one depth in the borehole;
      plotting the distribution of diffusion coefficients and the distribution of relaxation time constants as a cross-plot for the at least one depth;
      identifying a water line on the cross-plot, each point on the water line having substantially the same value for the diffusion coefficient; and
      estimating the distribution of pore sizes from the distribution of relaxation time constants plotted along the water line.

9. The apparatus of claim 8, wherein the relaxation time constants comprise transverse relaxation time constants and the electronics unit is further for determining a transverse relaxation time constant (COCBW) that separates clay bound water from irreducible water.

10. The apparatus of claim 8, wherein the relaxation time constants comprise transverse relaxation time constants and the electronics unit is further for determining a transverse relaxation time constant (COBVI) that separates irreducible water from movable water.

11. The apparatus of claim 10, wherein the electronics unit is further for determining free fluid volume by integrating an intrinsic transverse relaxation time constant component of the transverse relaxation time constant for values of the intrinsic transverse time constant component greater than COBVI for all values of the diffusion coefficient.

12. A non-transitory computer readable medium comprising computer executable instructions for estimating a distribution of pore sizes of a water and hydrocarbon filled rock formation by implementing a method comprising:

processing nuclear magnetic resonance (NMR) data to determine a distribution of diffusion coefficients and a distribution of relaxation time constants for the water and hydrocarbon filled rock formation for at least one depth in the borehole;

plotting the distribution of diffusion coefficients and the distribution of relaxation time constants as a cross-plot for the at least one depth;

identifying a water line on the cross-plot, each point on the water line having substantially the same value for the diffusion coefficient;

estimating the distribution of pore sizes from the distribution of relaxation time constants plotted along the water line; and at least one of recording the distribution of pore sizes and displaying the distribution of pore sizes to a user.

* * * * *